(12) United States Patent
Folan

(10) Patent No.: US 12,672,950 B2
(45) Date of Patent: Jul. 7, 2026

(54) SELF-ADJUSTING TISSUE LUMEN STENTS

(71) Applicant: Boston Scientific Scimed, Inc., Maple Grove, MN (US)

(72) Inventor: Martyn G. Folan, Loughrea (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 68 days.

(21) Appl. No.: 18/756,942

(22) Filed: Jun. 27, 2024

(65) Prior Publication Data

US 2025/0000634 A1 Jan. 2, 2025

Related U.S. Application Data

(60) Provisional application No. 63/510,783, filed on Jun. 28, 2023.

(51) Int. Cl.
*A61F 2/04* (2013.01)
*A61B 17/11* (2006.01)

(52) U.S. Cl.
CPC ............ *A61F 2/04* (2013.01); *A61B 17/1114* (2013.01); *A61F 2002/045* (2013.01); *A61F 2210/0014* (2013.01)

(58) Field of Classification Search
CPC .................. A61F 2/04; A61F 2002/041; A61F 2002/045; A61B 17/1114; A61B 2017/1139; A61B 2017/00606; A61M 27/002
See application file for complete search history.

(56) References Cited

U.S. PATENT DOCUMENTS

| | | | |
|---|---|---|---|
| 2018/0078745 A1* | 3/2018 | Gray .................. A61B 1/00101 |
| 2019/0254804 A1 | 8/2019 | Folan et al. |
| 2022/0079784 A1 | 3/2022 | Folan |
| 2022/0096253 A1 | 3/2022 | Tuck et al. |
| 2022/0203077 A1 | 6/2022 | Folan |

OTHER PUBLICATIONS

International Search Report and Written Opinion dated Oct. 4, 2024 for International Application No. PCT/US2024/035855.

* cited by examiner

*Primary Examiner* — Diane D Yabut
(74) *Attorney, Agent, or Firm* — Seager, Tufte & Wickhem, LLP

(57) ABSTRACT
The present disclosure provides medical devices such as self-expanding stents or tissue lumen stents with an overlapping layer. The medical devices can have a coating or cover disposed over all or a portion of the medical device. The overlapping layer define a doubled back portion at an end of the medical device that includes an elongate section to provide dynamic movement of the end of the medical device relative to a central portion of the medical device.

20 Claims, 11 Drawing Sheets

SELF-ADJUSTING TISSUE LUMEN STENTS

CROSS-REFERENCE TO RELATED APPLICATIONS

This application claims the benefit of U.S. Provisional Patent Application Ser. No. 63/510,783 filed on Jun. 28, 2023, the disclosure of which is incorporated herein by reference.

FIELD

This application relates generally to medical methods and devices. More specifically, the present disclosure relates to lumen stents and methods for their use in maintained lumen patency with medical procedures.

BACKGROUND

Tissue lumen stents are often used in medical procedures to maintain lumen patency. Typically, the tissue lumen stent has a body with upstream and downstream ends and a central region therebetween. Medical procedures can be provided, which include (a) accessing a biliary system of a patient with an endoscope, and (b) deploying, within the biliary system of the patient, a tissue lumen stent such that the tissue lumen stent contacts a lumen in the biliary system of the patient, such as, for example, the common bile duct, the pancreatic duct, and the hepatic duct.

BRIEF SUMMARY

Various embodiments described herein provide a tissue lumen stent with overlapping layers, at least one of which may comprise a coating or cover. Doubled back medical device designs are contemplated which combine benefits of covered stent drainage capabilities and uncovered stent retentive strength to promote tissue in-growth.

In some cases, when the stent is in the foreshortened configuration, the upstream flange structure has a larger maximum lateral dimension, axial width and/or axial radius than that of the downstream flange structure and may include an inclined portion having an axial length at least as long as a maximum diameter of the saddle region when the body is in the foreshortened configuration. On the other hand, some embodiments are characterized by a downstream flange structure that has a larger maximum lateral dimension, axial width and/or axial radius than that of the upstream flange structure. Alternatively, or additionally, the upstream flange structure can include a distal-most opening having a diameter larger than a maximum internal diameter of the saddle region when the body is in the foreshortened configuration. In certain embodiments, the body includes a covered mesh, and in some cases, may comprise both covered and uncovered mesh, while some embodiments include a covering or membrane over at least the cylindrical saddle portion of the stent and, optionally, one or both upstream and downstream flange structures.

Some embodiments of the disclosure can be implemented as a medical device. The medical device can comprise an elongate tubular body comprising a first end portion and a second end portion opposite the first end portion, the elongate tubular body having a constrained configuration and an unconstrained configuration; the first end portion, in the unconstrained configuration comprising a retention member, an elongate section distal to the retention member, and a doubled back portion extending from the elongate section over the retention member towards the second end portion.

In further embodiments of the medical device, the elongate tubular body can comprise a central portion disposed between the first end portion and the second end portion, the second end portion comprising a second retention member.

In further embodiments of the medical device, the second end portion can comprise a second doubled back portion extending from the retention member towards the first end portion.

In further embodiments of the medical device, the second end portion can comprise a second elongate section distal to the second retention member, wherein the second doubled back portion extends from the second elongate section over the second retention member towards the central portion.

In further embodiments of the medical device, the second end portion can comprise a straight end portion.

In further embodiments of the medical device, the second end portion can comprise a tapered end portion, the elongate tubular body comprising a central portion disposed between the first end portion and the tapered end portion.

In further embodiments of the medical device, the doubled back portion comprises a radial inner wall defining a lumen of the elongate tubular body and a radial outer wall extending over an outer perimeter of the inner wall.

In further embodiments of the medical device, the elongate tubular body can comprise a covering disposed over at least a portion of the elongate tubular body.

In further embodiments of the medical device, the elongate tubular body in the unconstrained configuration is configured to facilitate fluid flow without leakage between the first end portion and the second end portion.

In further embodiments of the medical device, the medical device is a self-expanding stent.

In further embodiments of the medical device, the elongate tubular body comprises a mesh, one or more braided wires, or woven filament.

In further embodiments of the medical device, the elongate tubular body comprises a polymer, a metal, a shape memory material, or Nitinol.

Some embodiments of the disclosure can be implemented as a medical device for placement in an anastomosis. The medical device can comprise an elongate tubular body comprising a first end portion and a second end portion opposite the first end portion, the elongate tubular body having a constrained configuration and an unconstrained configuration; the first end portion, in the unconstrained configuration comprising a retention member, an elongate section distal to the retention member, and a doubled back portion extending from the elongate section over the retention member towards the second end portion, wherein the elongate section is configured to provide dynamic movement of the retention member relative to the second end portion.

In further embodiments of the medical device, the elongate tubular body can comprise a central portion disposed between the first end portion and the second end portion, the second end portion comprising a second retention member and a second doubled back portion extending from the retention member towards the first end portion.

In further embodiments of the medical device, the second end portion can comprise a second elongate section distal to the second retention member, wherein the second doubled back portion extends from the second elongate section over the second retention member towards the central portion, and wherein the second elongate section is configured to provide dynamic movement of the second retention member relative to the first end portion.

Some embodiments of the disclosure can be implemented as a medical device. The medical device can comprise a stent comprising an elongate tubular body comprising a first end portion and a second end portion opposite the first end portion, the elongate tubular body having a constrained configuration and an unconstrained configuration; the first end portion, in the unconstrained configuration comprising a retention member, an elongate section distal to the retention member, and a doubled back portion extending from the elongate section over the retention member towards the second end portion; and a delivery device configured to hold the stent in the constrained configuration and deploy the stent in an anastomosis in the unconstrainted configuration.

BRIEF DESCRIPTION OF THE SEVERAL VIEWS OF THE DRAWINGS

To easily identify the discussion of any element or act, the most significant digit or digits in a reference number refer to the figure number in which that element is first introduced.

DETAILED DESCRIPTION

Figure 1A:
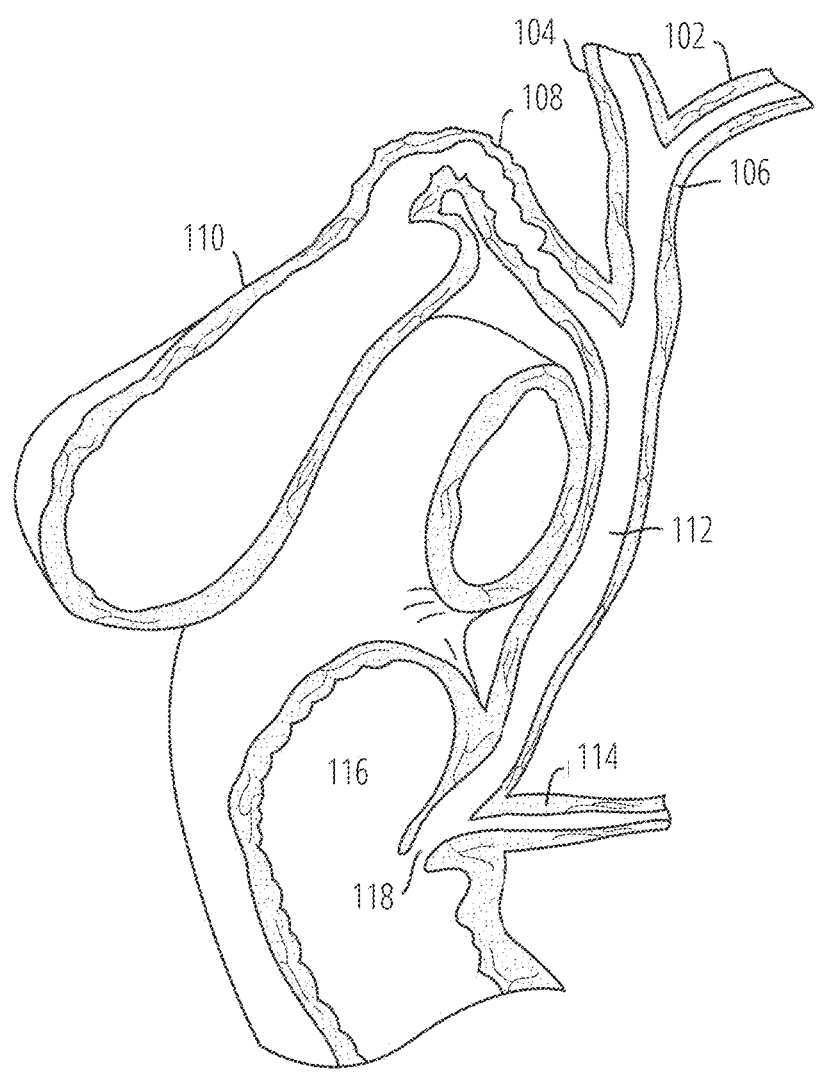
FIG. 1A illustrates a biliary system.

The present disclosure uses the terms anterograde, retrograde, downstream, upstream, proximal, distal, lower, upper, inferior, and superior to refer to various directions. Unless the context clearly indicates otherwise, the terms anterograde, downstream, proximal, lower, and inferior will generally be used synonymously to indicate a direction that is in line with fluid flow and along the devices and instruments toward the surgeon. Conversely, the terms retrograde, upstream, distal, upper, and superior will generally be used synonymously to indicate a direction that is against fluid flow and along the devices and instruments away from the surgeon. It should be noted, however, that this nomenclature is being defined here to help clarify the following descriptions rather than to limit the scope of the invention. While the exemplary embodiments disclosed herein focus on entry and placement in a retrograde direction, the disclosed methods, systems, and devices may in some circumstances be placed in an anterograde direction. In such situations, the "upstream" and "downstream" designations may be reversed.

As introduced above, the present disclosure described expandable stents used in the biliary system of a patient. As such a discussion of the biliary system is provided here. Bile, required for the digestion of food, is excreted by the liver into passages that carry the bile into the left hepatic duct 102 and the right hepatic duct 104. These two hepatic ducts merge to form the common hepatic duct 106. The common hepatic duct 106 exits the liver and joins the cystic duct 108 from the gallbladder 110, which stores bile, to form the common bile duct 112. The common bile duct 112, in turn, joins with the pancreatic duct 114 from the pancreas to feed bile, pancreatic juice and insulin into the descending part of the duodenum 116 through the ampulla of Vater 118. A sphincter, known as the sphincter of Oddi, is located at the opening of the ampulla of Vater 118 into the duodenum 116 to prevent matter in the duodenum 116 from traveling in a retrograde direction up into the common bile duct 112.

Tumor growth, hyperplasia, pancreatitis, or other strictures in or around the biliary duct tree outlined above can impede or block the flow of fluid from the liver, gallbladder and/or pancreas to the duodenum. To alleviate the effects of the stricture, a stent may need to be placed in a portion of the biliary system. The stent may be placed endoscopically. One procedure for placing the stent is endoscopic retrograde cholangiopancreatography (ERCP). ERCP is a technique that combines the use of endoscopy and fluoroscopy to diagnose and treat certain problems of the biliary or pancreatic ductal systems. The procedure involves placing an endoscope down the esophagus, through the stomach, into the duodenum, then passing various accessories through the endoscope instrumentation channel up through the ampulla of Vater into the biliary or pancreatic ductal systems. Alternatively, a special slim-diameter endoscope, sometimes referred to as a peroral cholangioscope, may be passed directly into the bile or pancreatic ducts.

Thus, stents currently placed by ERCP are used to facilitate drainage of bile through the biliary tree. Drainage is a commonly expressed desire for self-expanding stents, allowing residual drainage from secondary sources. The present disclosure describes and depicts several self-expanding stents with improved drainage features or characteristics.

Figure 1B:
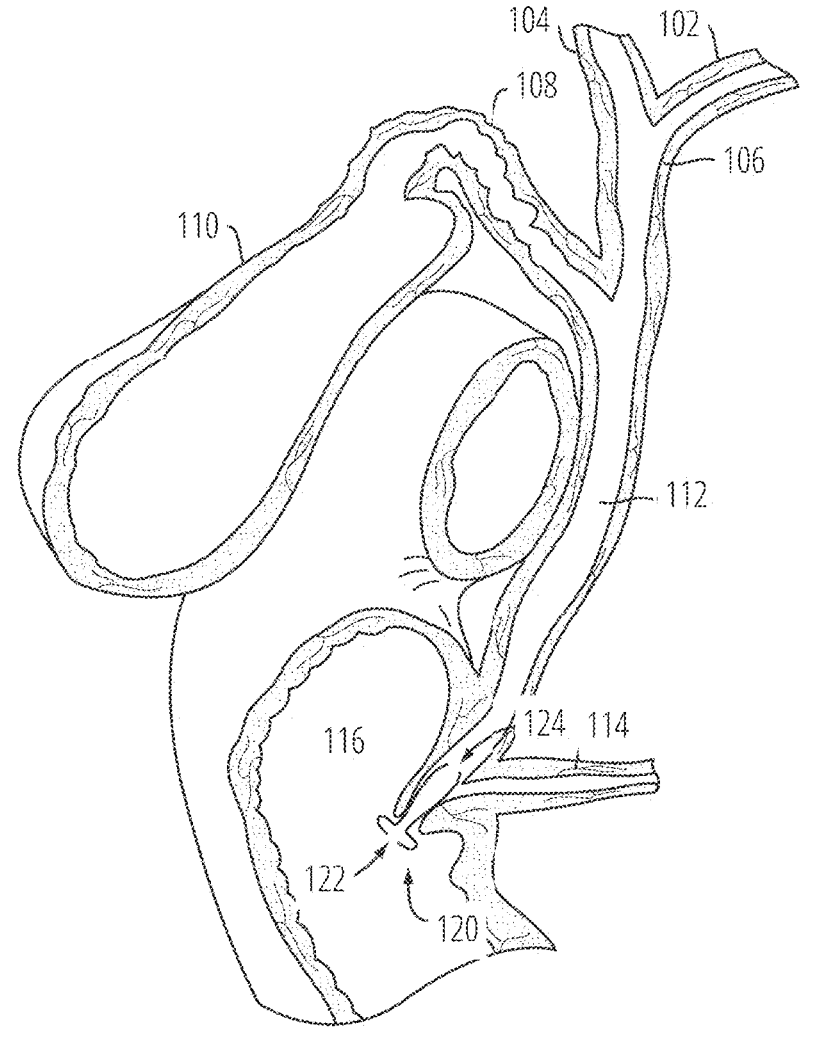
FIG. 1B illustrates the biliary system of FIG. 1A with a stent placed therein.

FIG. 1B illustrates an exemplary biliary stent 120 implanted in the lower end of the common bile duct 112. In such a configuration, stent 120 may be used to treat an ampullary stenosis. In other embodiments, the stent 120 may be longer to bridge a bile duct stricture higher upstream. Stent 120 comprises a downstream end 122 that protrudes into the duodenum 116, and an upstream end 124 that extends up into the common bile duct 112. Stent 120 is shown in a generally radially expanded and axially foreshortened state, such that it is contacting the walls of the common bile duct 112 continuously along its length, or at least in several places.

Although embodiments of the present disclosure are described with specific reference to medical devices (e.g., anastomotic devices, stents, etc.) and methods for drainage of (or access to) the biliary system, it should be appreciated that such medical devices and methods may be used in a variety of medical procedures (e.g., external biliary drain conversion, enteroenterostomy, gastrojejumostomy, gastroduodenostomy and gastroileostomy, etc.) to establish and/or maintain a temporary or permanent open flow passage between or drainage from a variety of body organs, ducts, lumens, vessels, fistulas and spaces (e.g., the dermis, stomach, duodenum, gallbladder, bladder, kidneys, walled off pancreatic necrosis (WOPN), abscesses, etc.). The devices can be inserted via different access points and approaches, (e.g., percutaneously, endoscopically, laparoscopically or some combination). Various stents described are self-expanding stents, but other embodiments where the stent is expandable by other means, for example, a balloon catheter, may be possible. Moreover, such medical devices are not limited to drainage, but may facilitate access to organs, vessels, or body lumens for other purposes, such as creating a path to divert or bypass fluids or solids from one location to another, removing obstructions and/or delivering therapy, including non-invasive manipulation of the tissue within the organ and/or the introduction of pharmacological agents via the open flow passage. In some embodiments, devices, systems, and methods may comprise one or more similarities to the Drawings and/or Specification of United States Patent Application Publication No. 2019/0254804, titled "DRAINAGE DEVICE" filed on Feb. 19, 2019, which is presently incorporated by reference herein in its entirety.

Figures 2A, 2B:
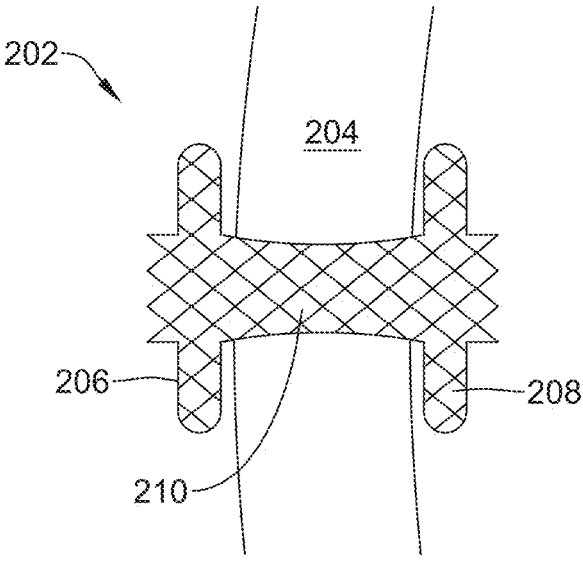
FIG. 2A and FIG. 2B illustrate a stent placed in an anastomosis of a tissue wall.

As noted, stents (e.g., stent 120, or the like) can be used to facilitate transgastric or transduodenal endoscopic drainage of both attached and detached conditions. For example, a stent can be placed to treat a pancreatic pseudocyst, a walled-off necrosis, or gallbladder in patients with acute cholecystitis of the bile duct after a failed ERCP. Further, stents can be used to for gastric-to-small intestine channeling procedures, such as, an endoscopic ultrasound (EUS) guided gastrojejunostomy. FIG. 2A and FIG. 2B illustrate a stent 202 placed across a cyst wall 204. The stent 202 is a hollow bodied stent having opposing flanges 206 and 208 separated by a saddle 210. The flanges 206 and 208 are double wall flanges extending perpendicular to the saddle 210. Stents designed like stent 202 are advantageous as the flanges 206 and flange 208 can readily be visualized and provide an indication of the length of the saddle 210 which indicates the maximum distance to be crossed (or bridged by the stent). FIG. 2A depicts the stent crossing the tissue of a cyst wall 204, which can be placed to provide drainage to the cyst.

Although the design of stents like stent 202 have certain advantages, there can be problems if the stent is placed incorrectly or if the tissue wall expands (e.g., due to post procedure inflammation, or the like). For example, if the tissue wall width 212 is substantially larger than the saddle width 214, one or both flanges 206 and 208 can deform. For example, FIG. 2B illustrates flange 206 deformed into a "goblet" shape. Such deformation can lead to complications such as, for example, stent migration.

Figure 3A:
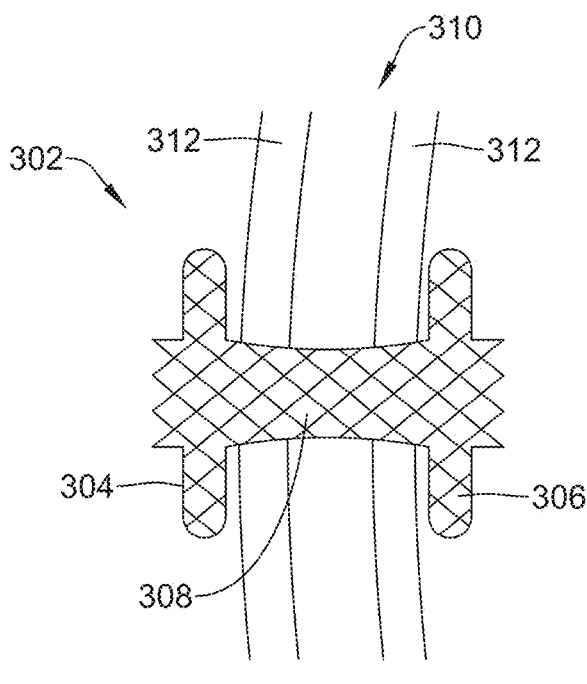
FIG. 3A and FIG. 3B illustrate a stent placed in an anastomosis of unattached tissue walls.

As noted, stents can be used to bridge two unattached structures (e.g., the duodenum and gallbladder, or a gastric-duodenum bypass). FIG. 3A illustrates a stent 302 placed across unattached tissue vessel walls 312. The vessel walls 312 can, for example, be separated by peritoneum 310. The stent 302 is a hollow bodied stent having opposing flanges 304 and 306 separated by a saddle 308. The flanges 306 and 308 are double wall flanges extending perpendicular to the saddle 308. It is to be appreciated that in instances where unattached vessels are being bridged, as the regions have potential independent mobilities stent migration may be a particularly problematic issue.

Figure 3B:
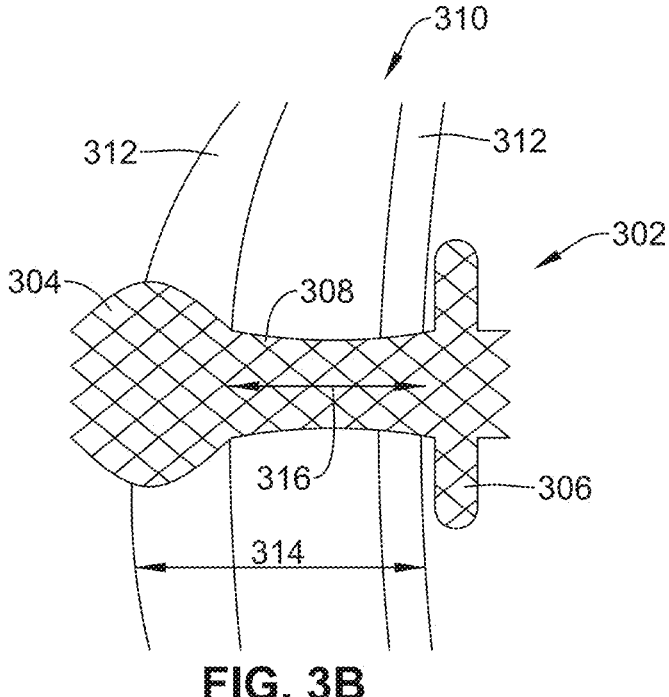

For example, where the distance to be bridged 314 is greater than the saddle width 316 (e.g., due to misplacement, tissue movement, or the like), one or both flanges 304 and 306 can deform. FIG. 3B illustrates flange 304 deformed into a "goblet" shape. Such deformation can lead to complications such as, for example, stent migration.

Figure 4:
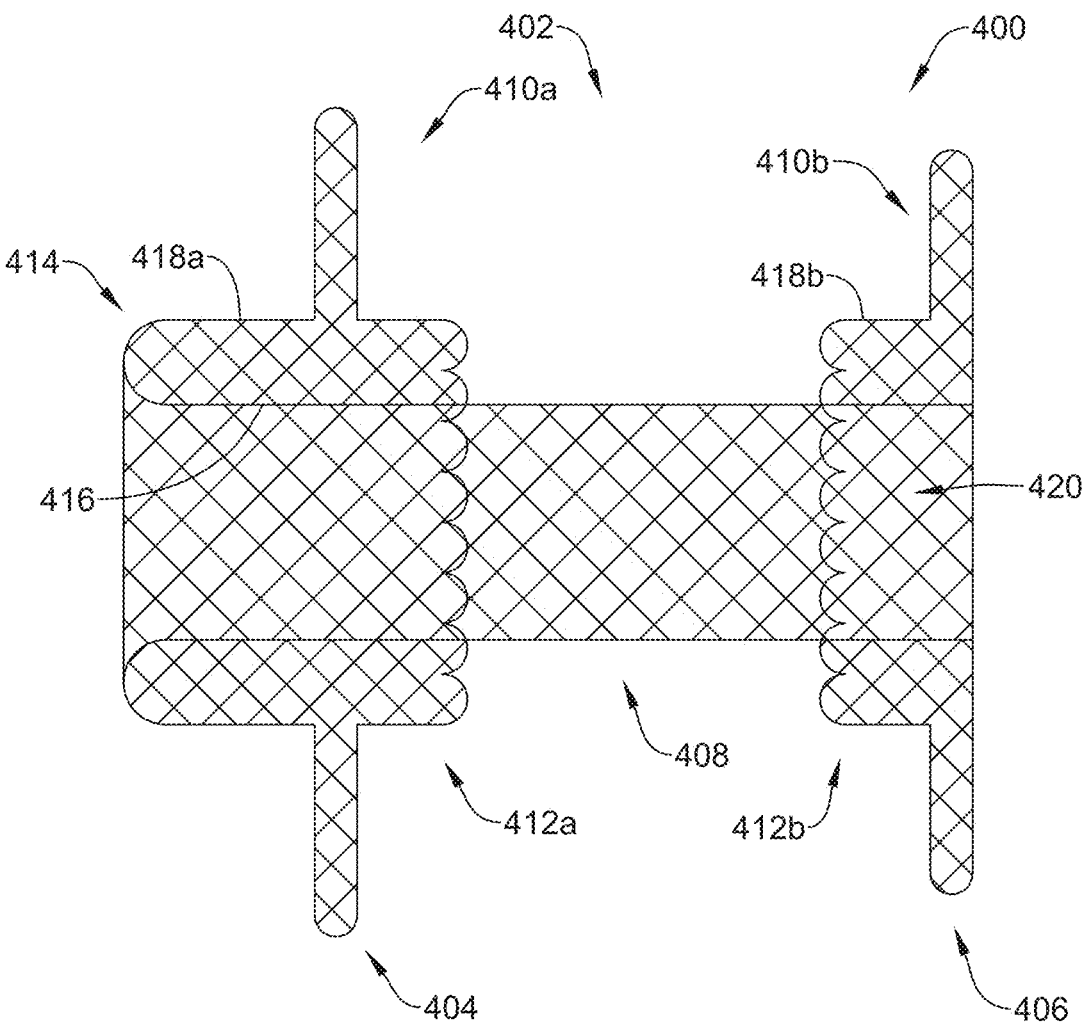
FIG. 4 illustrates a side view of a first example medical device in accordance with at least one embodiment of the disclosure.

FIG. 4 illustrates a side view of an exemplary medical device 400 according to various embodiments described herein. Medical device 400 (e.g., stent, or drainage stent) may include an elongate tubular body 402 configured to move between a first (e.g., constrained, collapsed, non-expanded) configuration and a second (e.g., non-constrained, expanded) configuration. For the sake of brevity, a "first configuration" as referred to herein will be understood to collectively refer to a constrained configuration, collapsed configuration, non-expanded configuration or the like, while a "second configuration" as referred to herein will be understood to collectively refer to a constrained configuration, collapsed configuration, compressed configuration, non-expanded configuration, or the like. Embodiments, however, are not limited in this context.

The elongate tubular body 402 may comprise a mesh, one or more braided wires, or woven filament (not shown), which may be formed of a polymer, metal, or other material. In many embodiments, the elongate tubular body 402 may be formed of a shape memory material, such as Nitinol or similar alloy. For the sake of simplicity, the present disclosure may refer to a material of a stent as a woven filament or plurality of woven filaments, but embodiments may alternatively and/or additionally comprise other materials and/or configurations of filament.

The elongate tubular body 402 may comprise a first end portion 404 (e.g., a proximal or proximal end portion, region, or section) and an opposite second end portion 406 (e.g., a distal or distal end portion, region, or section), and a central portion 408 (e.g., a saddle or central saddle portion, region, or section) extending therebetween. The elongate tubular body 402 may define a lumen 420 extending longitudinally therethrough.

The first end portion 404 may comprise a retention member 410a and an elongate section 414 extending distal from the retention member 410a away from the second end portion 406. The first end portion 404 may further include an overlap portion 412a which extends from the elongate section 414 over the retention member 410a and towards the second end portion 406. The second end portion 406 may comprise a retention member 410b and an overlap portion 412b which extends from the retention member 410b towards the first end portion 404. The overlap portion 412a and 412b may comprise a radially inner wall 416. Further, the overlap portion 412a may comprise outer wall 418a while overlap portion 412b may comprise outer wall 418b.

Central portion 408 may be continuously formed with one or both of first end portion 404 and second end portion 406. For example, central portion 408 can be continuously formed with radial inner wall 416, outer wall 418a, retention member 410a and/or outer wall 418b and retention member 410b. In many embodiments, first end portion 404, central portion 408, and second end portion 406 can be formed from a single elongate frame or member, wherein elongate section 414, retention members 410a and 410b and/or overlap portions 412a and 412b are formed by doubling back a portion of the single elongate frame or member over an adjacent portion of the single elongate frame or member so that an inner cylindrical body (e.g., radially inner wall 416, or radially inner wall 416 together with central portion 408) is disposed within and/or disposed to extend through a portion of an outer cylindrical body (e.g., radially outer wall outer walls 418a and 418b). Accordingly, elongate section 414 as well as retention members 410a and 410b may be formed by a portion of a doubled-back woven filament.

It is to be appreciated that conventional medical devices with double wall retention members (e.g., like first end portions 404 and 406) can act as a reservoir area that may become a site of fluid and/or sludge build-up. The medical device 400 of the present disclosure, however, provides an advantage in that inner wall 416 covers the first end portions 404 and 406 and mitigates this reservoir effect.

Figure 5:
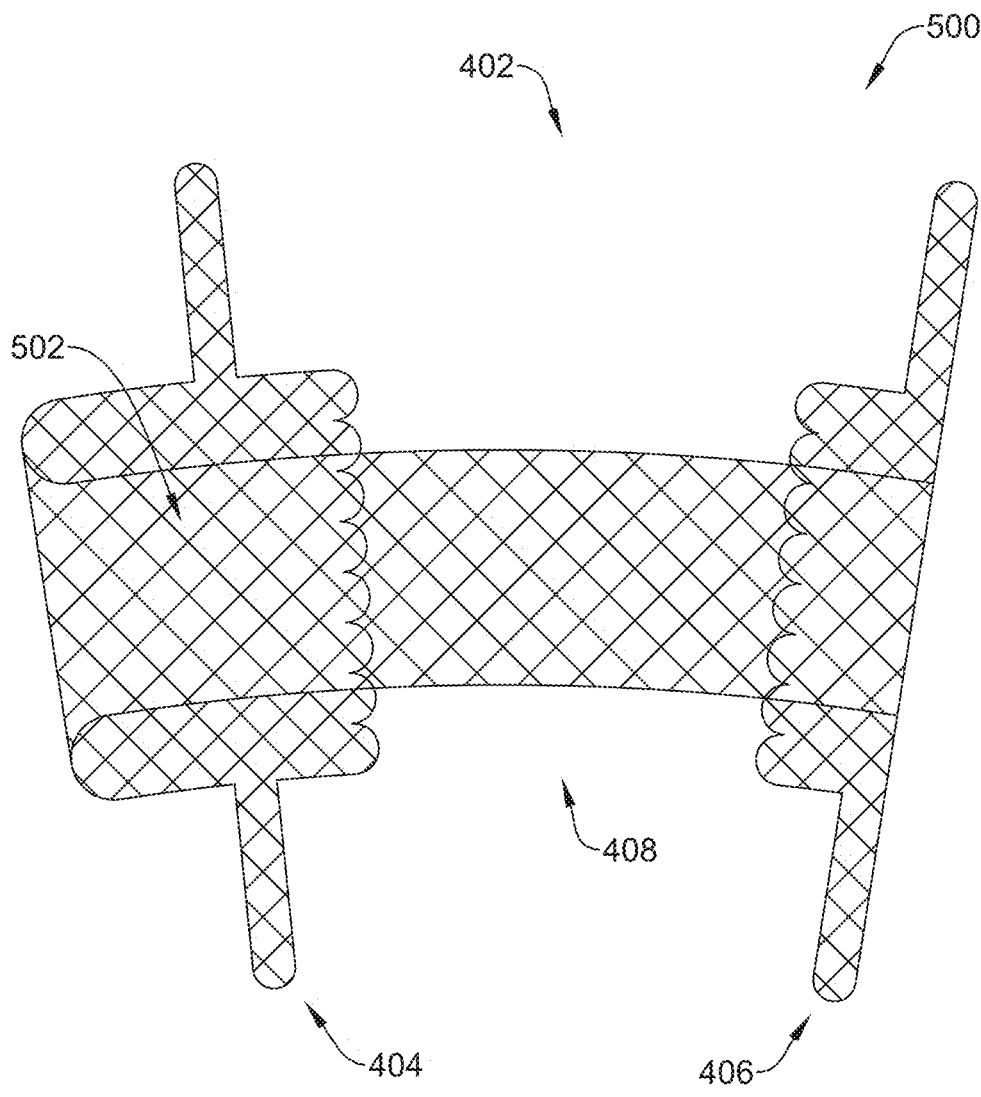
FIG. 5 illustrates a side view of a second example medical device in accordance with at least one embodiment of the disclosure.

FIG. 5 illustrates a view of an exemplary medical device 500 according to various embodiments described herein. Medical device 500 may be like medical device 400 and include elongate tubular body 402, first end portion 404, second end portion 406, and central portion 408. Additionally, elongate tubular body 402 may comprise a coating or cover 502 extending at least partially along an axial length thereof. Cover 502 may comprise silicone, urethane, Chronoflex, polytetrafluoroethylene (PTFE), or other suitable material.

The doubled-back configuration of medical device 400 and medical device 500 depicted in FIG. 4 and FIG. 5, including overlap portions 412a and 412b may provide various benefits over conventional designs. For example, the layering of radially inner wall 416 and radially outer walls 418a and 418b may provide stability or mechanical rigidity to overlap portions 412a and 412b. The doubled-back configuration of retention members 410a and 410b may increase a retentive force of the medical device 400 compared to corresponding retention members that do not include such a doubled-back configuration. For example, for the medical device 400 to migrate, retention members 410a and 410b as supported by radially inner wall 416 and radially outer walls 418a and 418b would have to deform, which may be less likely due to its doubled back geometry. One or both of radially inner wall 416 and radially outer walls 418a and 418b can resist or oppose a deformation of retention members 410a and 410b, thereby resulting in a greater pull-out force of the medical device 400 as opposed to alternative designs.

Medical device 400 and medical device 500 provides further advantages over conventional designs in that the elongate section 414 provides a suspension functionality. This manifests itself in that any separation of the independent vessel regions (e.g., vessel walls 312 moving apart, or the like) can be accommodated by the shortening of the elongated region as it becomes part of the true saddle while the flanges retain their overall shape and resistance to the vessel walls without an increase on the applied pressure. As such, the elongated elongate section 414 acts as a material reservoir that can be utilized to lengthen or shorten the central portion 408 as needed.

Figure 6A:
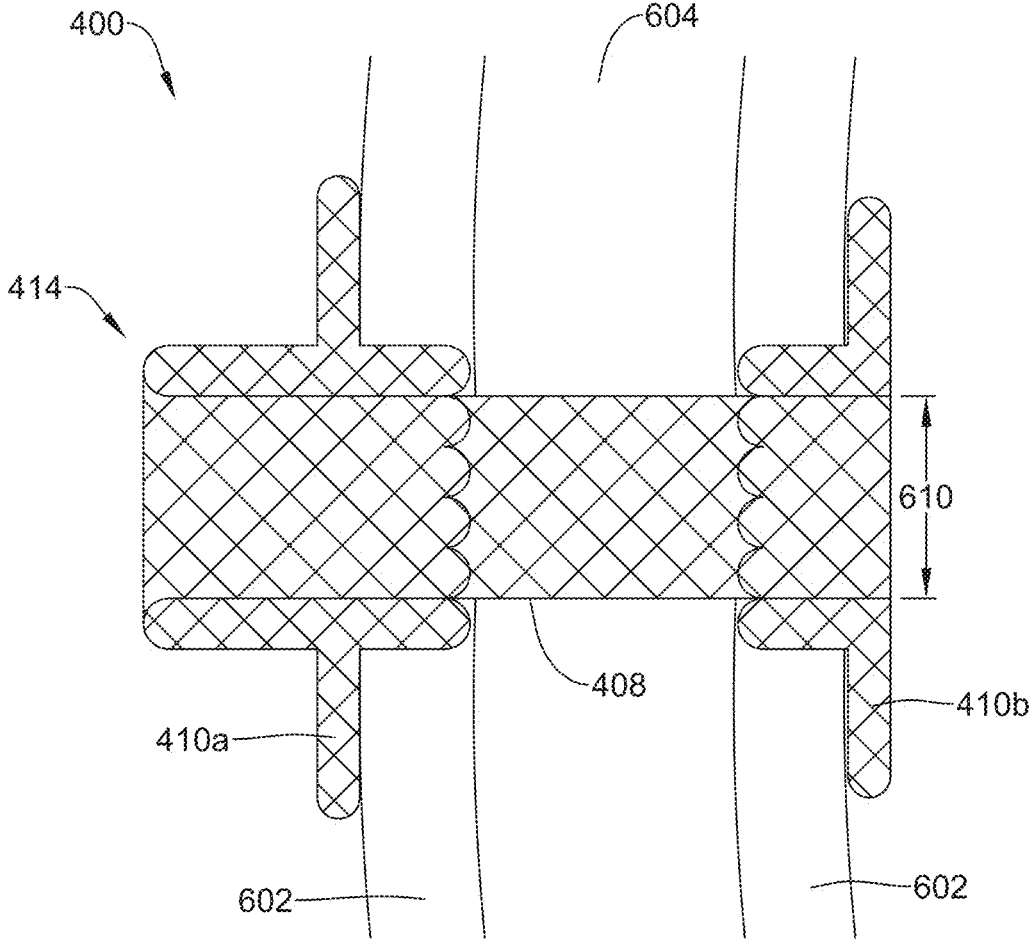
FIG. 6A illustrates the medical device of FIG. 4 placed in an anastomosis of unattached tissue walls.
Figures 6B, 6C:
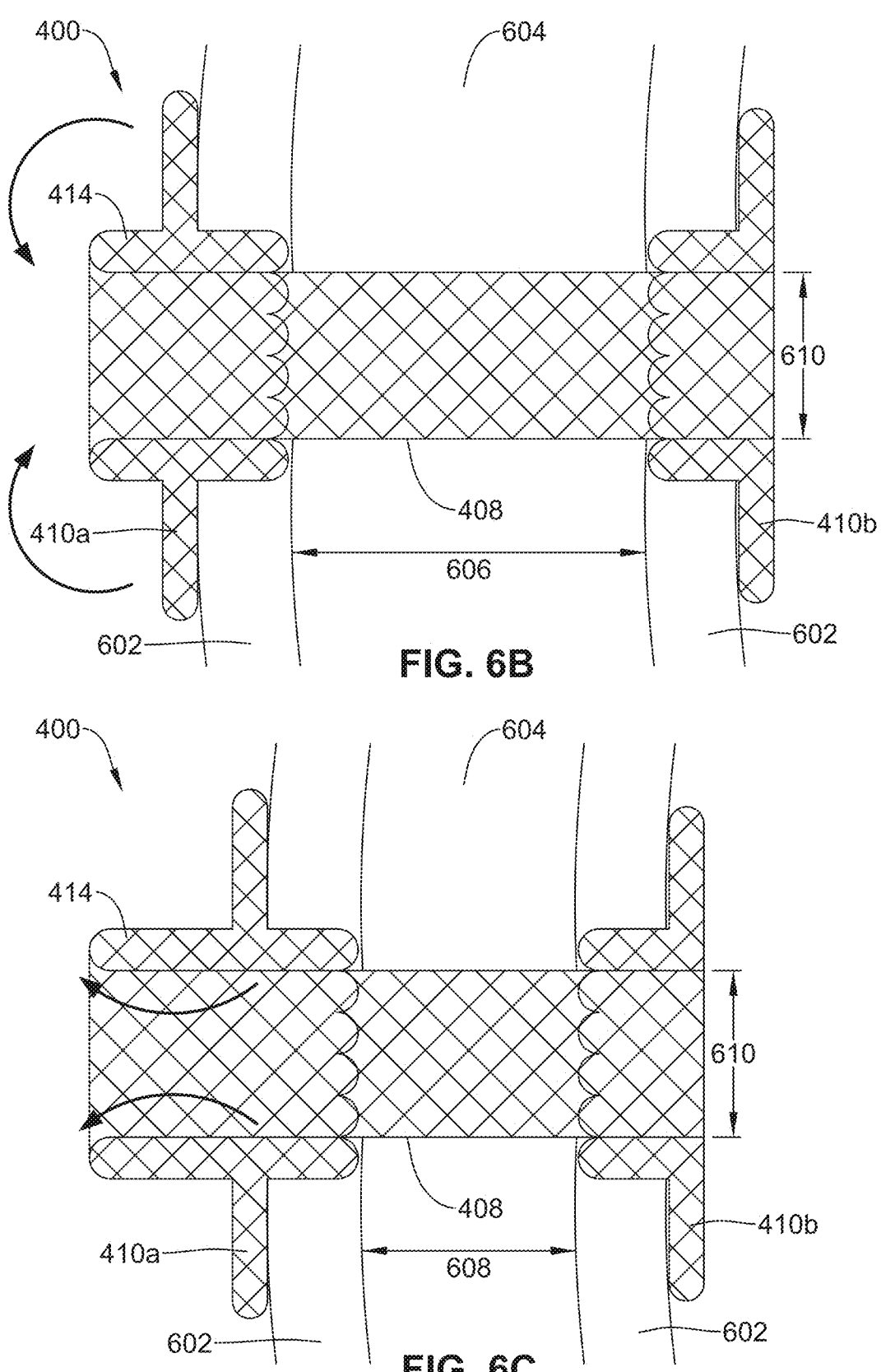
FIG. 6B and FIG. 6C illustrate the medical device placed in the anastomosis of FIG. 6A during movement of the tissue walls.

FIG. 6A, FIG. 6B, and FIG. 6C illustrates the above described suspension features of a medical device implemented according to the present disclosure. These figures use medical device 400 to describe this functionality. However, the concepts apply to medical device 500 as well as other medical devices implemented according to the present disclosure. FIG. 6A illustrates medical device 400 bridging unattached vessel walls 602, which are separated by peritoneum 604. The retention member 410a and retention member 410b engage opposing walls of peritoneum 604 with elongate section 414 acting as a reservoir to reduce or lengthen the central portion 408 width to accommodate a change in the width of the bridged vessel walls 602.

For example, FIG. 6B illustrates a widening of the peritoneum 604, which with conventional stents could result in a migration or pull out of the retention members. However, elongate section 414 of medical device 400 can be reduced or be "taken up" or used by central portion 408 to accommodate the increased width 606 of peritoneum 604 and provides that retention member 410a and retention member 410b may retain their shape and holding or retention force against vessel walls 602.

FIG. 6C illustrates a shortening of the peritoneum 604, which with conventional stents could also result in a migration due to the reduction in contact of the retention members of the opposing tissue walls. However, elongate section 414 of medical device 400 can be increased or "take up" a portion of central portion 408 to accommodate the decreased width 608 of peritoneum 604 and provide that retention member 410a and retention member 410b may retain their shape and holding or retention force against vessel walls 602.

An added advantage to the elongate section 414 taking up or providing "slack" to/from the central portion 408 is that the central portion 408 can maintain a substantially constant diameter 610 over the lifetime usage of the device. For example, FIG. 6A to FIG. 6C show the diameter 610 remaining substantially constant despite changes in the length of the central portion 408. As will be appreciated, conventional devices may experience a reduction in the diameter of the central portion saddle portion as the retention members are stretched apart due to expansion or movement of the opposing tissue walls. As the medical devices contemplated herein have a primary use of supplying a drainage path, this reduction in the diameter of the central portion may lead to premature occlusion of the lumen of the medical device.

Figure 7:
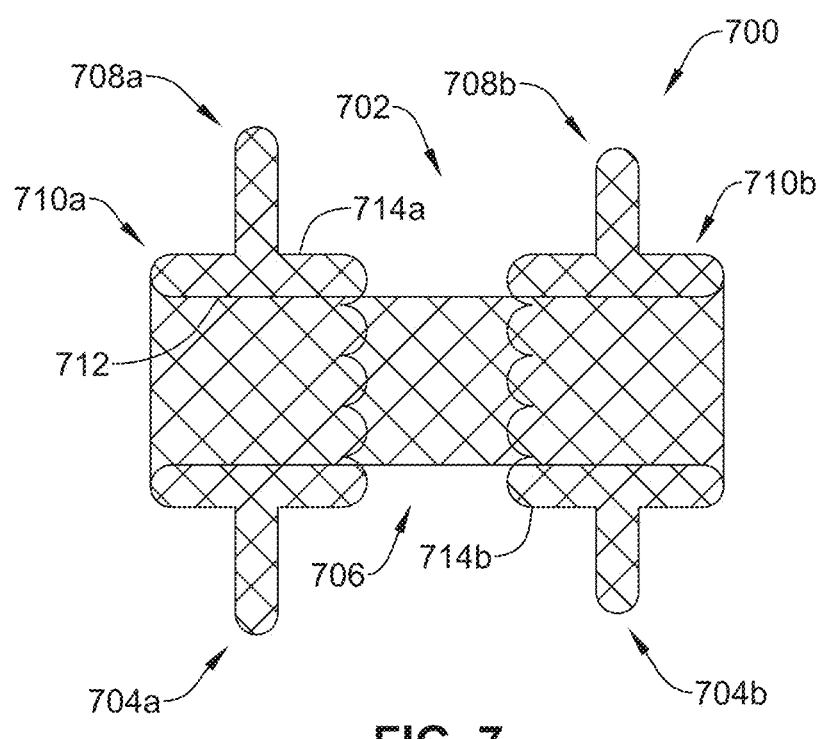
FIG. 7 illustrates a side view of a third example medical device in accordance with at least one embodiment of the disclosure.

FIG. 7 illustrates a side view of an exemplary medical device 700 according to various embodiments described herein. Medical device 700 (e.g., stent, or drainage stent) may include an elongate tubular body 702 configured to move between a first configuration and a second configuration. The elongate tubular body 702 may comprise a mesh, one or more braided wires, or woven filament, which may be formed of a polymer, metal, or other material. In many embodiments, the elongate tubular body 702 may be formed of a shape memory material, such as Nitinol or similar alloy. Further, all or a portion of elongate tubular body 702 may be covered (e.g., like medical device 500 of FIG. 5).

The elongate tubular body 702 may comprise a first end portion 704a (e.g., a proximal or proximal end portion, region, or section) and an opposite second end portion 704b (e.g., a distal or distal end portion, region, or section), and a central portion 706 (e.g., a saddle or central saddle portion, region, or section) extending therebetween. The elongate tubular body 702 may define a lumen extending longitudinally therethrough.

The first end portion 704a and second end portion 704b may comprise retention members 708a and 708b as well as elongate sections 710a and 710b, respectively. Further, each of first end portion 704a and second end portion 704b may further include an overlap or fold-back portion which extends from the elongate sections 710a and 710b over the retention members 708a and 708b towards the central portion 706. The overlap or fold-back portion may be defined by a radial inner wall 712 and radial outer walls 714a and 714b.

Figure 8:
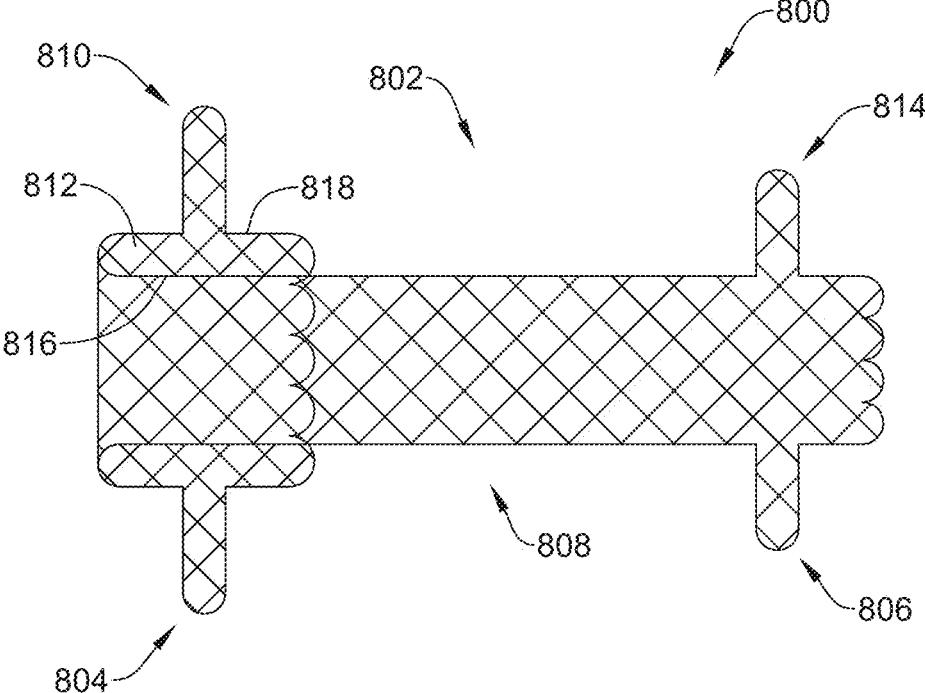
FIG. 8 illustrates a side view of a fourth example medical device in accordance with at least one embodiment of the disclosure.

FIG. 8 illustrates a side view of an exemplary medical device 800 according to various embodiments described herein. Medical device 800 (e.g., stent, or drainage stent) may include an elongate tubular body 802 configured to move between a first configuration and a second configuration. The elongate tubular body 802 may comprise a mesh, one or more braided wires, or woven filament, which may be formed of a polymer, metal, or other material. In many embodiments, the elongate tubular body 802 may be formed of a shape memory material, such as Nitinol or similar alloy. Further, all or a portion of elongate tubular body 802 may be covered (e.g., like medical device 500 of FIG. 5).

The elongate tubular body 802 may comprise a first end portion 804 (e.g., a proximal or proximal end portion, region, or section) and an opposite second end portion 806 (e.g., a distal or distal end portion, region, or section), and a central portion 808 (e.g., a saddle or central saddle portion, region, or section) extending therebetween. The elongate tubular body 802 may define a lumen extending longitudinally therethrough.

The first end portion 804 may comprise retention member 810 and elongate section 812. Further, first end portion 804 may include an overlap or fold-back portion which extends from the elongate section 812 over the retention member 810 towards the central portion 808. The overlap or fold-back portion may be defined by a radial inner wall 816 and radial outer wall 818.

The second end portion 806 may comprise a retention member 814. As depicted, the second end portion 806 does not include an overlap or fold-back portion.

Figure 9:
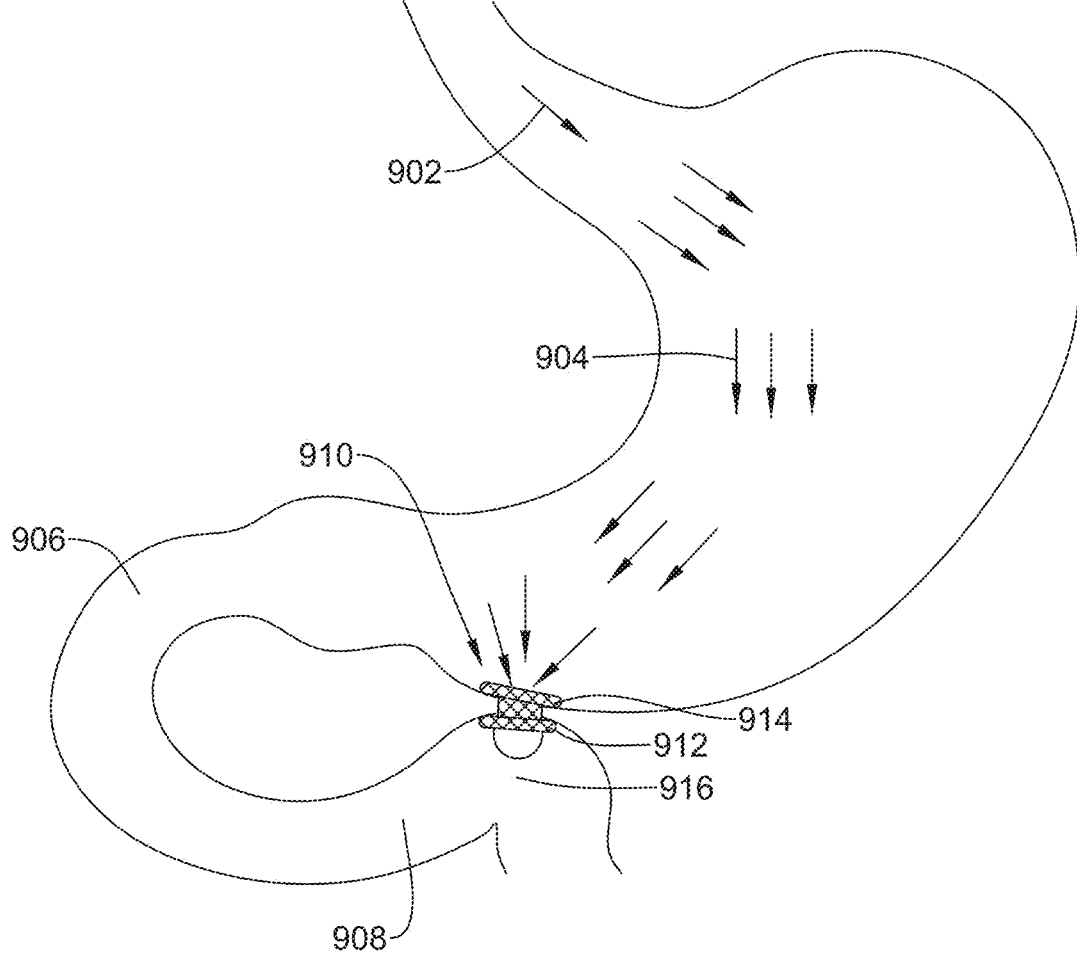
FIG. 9 illustrates a medical device in accordance with at least one embodiment of the disclosure placed in a gastrojejunostomy (GJ) configuration.

FIG. 9 illustrates an example placement of medical devices implemented according to the present disclosure. This figure illustrates an esophagus 902, stomach 904, small intestine 906, and duodenum 908. Further illustrated is a medical device 910, which can be like the medical device 400 of FIG. 4 or medical device 500 or FIG. 5. Medical device 910 includes retention members 912 and 914 as well as an elongated elongate section 916. The medical device 910 is placed in a traditional gastrojejunostomy (GJ) configuration with the retention member 912 and elongate section 916 disposed in the duodenum 908. As such, the retention member 912 contacts the tissue walls of the duodenum 908 and the retention member 914 contacts the tissue walls of the stomach 904, thus bridging the anastomosis created between these two opposing unattached tissue walls. It is to be appreciated that the tissue walls of the duodenum 908 and stomach 904 may not be perpendicular. Conventional medical devices used in GJ procedures are maximized for perpendicular retention members to contact tissue walls, which form a concentric contact region at the anastomosis point. As such, any non-perpendicular, eccentric, or other non-concentricity at the location of the anastomosis may form a region of poor apposition or non-contact.

However, the medical devices of the present disclosure (e.g., medical device 400, medical device 500, medical device 910, etc.) provide that the elongated section (e.g., elongate section 414, elongate section 916, etc.) can move in multiple directions allowing for non-perpendicular regions to be better opposed by the retention members. As such, angulation between the opposing tissue walls may not result in a non-contact situation. Such "spring" like movement of the elongate section 916 can happen dynamically while the device is in use, for example to accommodate movement of the patient, or the like.

A further advantage of the medical devices of the present disclosure over conventional devices, particularly when deployed in the GJ configuration as shown in FIG. 9 is that the dynamic elongated elongate section 916 may aid in preventing food impaction on the device lumen as the movement of the elongated elongate section 916 within the duodenum 908 can cause the food to be repeatably dislodged from the lumen.

Figure 10:
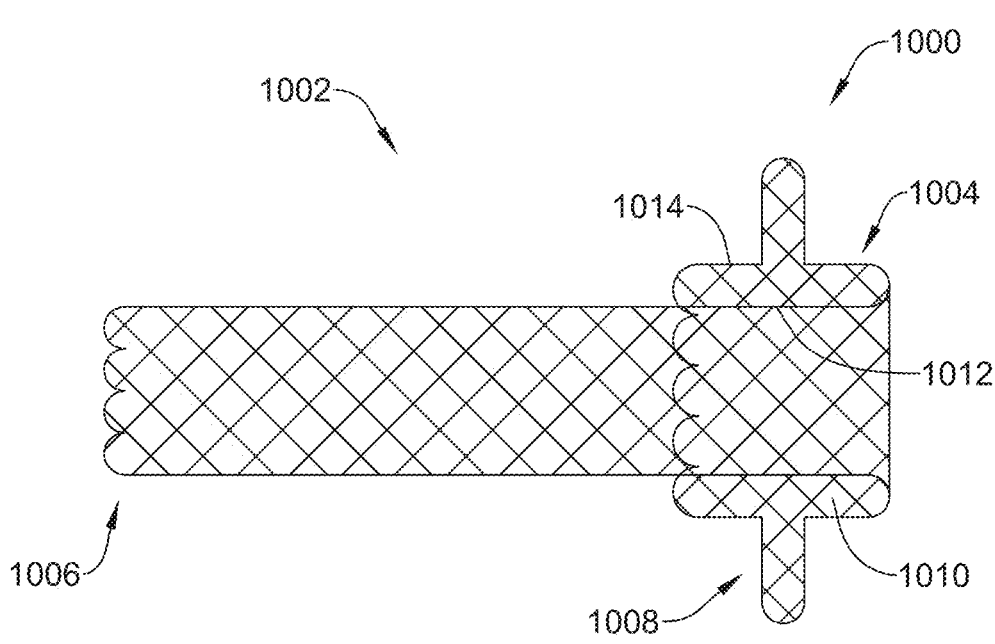
FIG. 10 illustrates a side view of a fifth example medical device in accordance with at least one embodiment of the disclosure.
Figure 11:
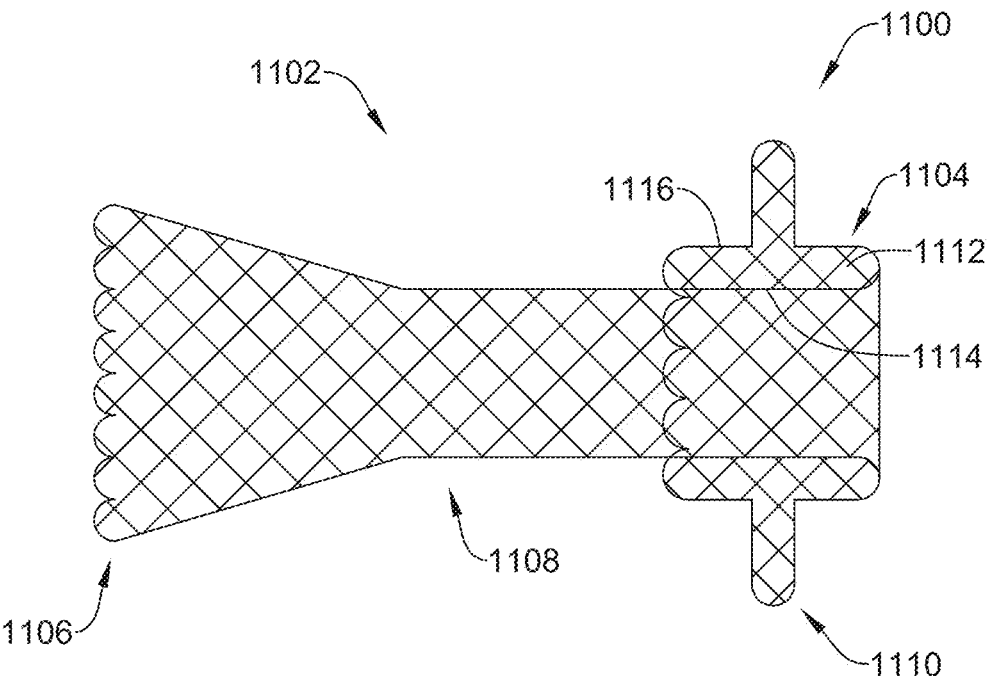
FIG. 11 illustrates a side view of a sixth example medical device in accordance with at least one embodiment of the disclosure.

Medical devices can be implemented based on the present disclosure to provide a device configured for hepaticogastrostomy (HGS) procedures and HGS configurations. HGS configurations provide that a medical device is placed to span the non-connected gastric region to the hepatic vessels across the peritoneal cavity. It is to be appreciated that some degree of independent mobility in both organs is expected. FIG. 10 and FIG. 11 illustrate medical devices that can be used in an HGS configuration while providing for the above noted degree of flexibility.

FIG. 10 illustrates a side view of an exemplary medical device 1000 according to various embodiments described herein. Medical device 1000 (e.g., stent, or drainage stent) may include an elongate tubular body 1002 configured to move between a first configuration and a second configuration. The elongate tubular body 1002 may comprise a mesh, one or more braided wires, or woven filament, which may be formed of a polymer, metal, or other material. In many embodiments, the elongate tubular body 1002 may be formed of a shape memory material, such as Nitinol or similar alloy. Further, all or a portion of elongate tubular body 1002 may be covered (e.g., like medical device 500 of FIG. 5).

The elongate tubular body 1002 may comprise a first end portion 1004 (e.g., a proximal or proximal end portion, region, or section) and a straight end portion 1006 extending from the first end portion 1004. The elongate tubular body 1002 may define a lumen extending longitudinally therethrough.

The first end portion 1004 may comprise retention member 1008 and elongate section 1010. Further, first end portion 1004 may include an overlap or fold-back portion which extends from the elongate section 1010 over the retention member 1008 towards the straight end portion 1006. The overlap or fold-back portion may be defined by a radial inner wall 1012 and radial outer wall 1014.

FIG. 11 illustrates a side view of an exemplary medical device 1100 according to various embodiments described herein. Medical device 1100 (e.g., stent, or drainage stent) may include an elongate tubular body 1102 configured to move between a first configuration and a second configuration. The elongate tubular body 1102 may comprise a mesh, one or more braided wires, or woven filament, which may be formed of a polymer, metal, or other material. In many embodiments, the elongate tubular body 1102 may be formed of a shape memory material, such as Nitinol or similar alloy. Further, all or a portion of elongate tubular body 1102 may be covered (e.g., like medical device 500 of FIG. 5).

The elongate tubular body 1102 may comprise a first end portion 1104 (e.g., a proximal or proximal end portion, region, or section) and an opposite tapered end portion 1106 (e.g., a distal or distal end portion, region, or section), and a central portion 1108 (e.g., a saddle or central saddle portion, region, or section) extending therebetween. The elongate tubular body 1102 may define a lumen extending longitudinally therethrough.

The first end portion 1104 may comprise retention member 1110 and elongate section 1112. Further, first end portion 1104 may include an overlap or fold-back portion which extends from the elongate section 1112 over the retention member 1110 towards the tapered end portion 1106. The overlap or fold-back portion may be defined by a radial inner wall 1114 and radial outer wall 1116.

The medical devices medical devices 1000 and 1100 of FIG. 10 and FIG. 11 include elongate sections (e.g., elongate sections 1010 and 1112, etc.) that provide the above described suspension effects to prior or conventional HGS designs. As such, the medical devices of the present disclosure when deployed in an HGS configuration could overcome the motion between the connected organs and lead to a more stable deployed device. Accordingly, it is contemplated that the ends with the elongated elongate sections 1010 and 1112 are placed on the gastric side while the static end (e.g., straight end portion 1006 or tapered end portion 1106) are placed in the hepatic region. As previously described, the additional length due to the elongate sections on the gastric side could aid in retrograde flow or food impaction and the motion of the elongated section can aid in keeping the lumen clear by ejecting potential food accumulation on the gastric side.

Although the medical devices 400, 500, 700, 800, 1000, and 1100 disclosed herein are generally depicted as including woven, knitted, or braided filaments (e.g., Nitinol, etc.), in various embodiments, the medical devices may include laser cut designs which may or may not change in length (e.g., shorten) as the medical device moves from the first configuration to the second configuration. The medical devices in various configurations may be self-expanding or expandable such as balloon-expandable.

What is claimed is:

1. A medical device, comprising:
an elongate tubular body comprising a first end portion, a body portion, and a second end portion opposite the first end portion, the elongate tubular body having a constrained configuration and an unconstrained configuration;
the first end portion, in the unconstrained configuration comprising a retention member, an elongate section distal to the retention member, and a doubled back portion extending from the elongate section over the retention member towards the second end portion; and
wherein the doubled back portion has a free proximal end unattached to the body portion of the elongate tubular body.

2. The medical device of claim 1, the elongate tubular body comprising a central portion disposed between the first end portion and the second end portion, the second end portion comprising a second retention member.

3. The medical device of claim 2, the second end portion comprising a second doubled back portion extending from the retention member towards the first end portion.

4. The medical device of claim 3, the second end portion comprising a second elongate section distal to the second retention member, wherein the second doubled back portion extends from the second elongate section over the second retention member towards the central portion.

5. The medical device of claim 1, the second end portion comprising a straight end portion.

6. The medical device of claim 1, the second end portion comprising a tapered end portion, the elongate tubular body comprising a central portion disposed between the first end portion and the tapered end portion.

7. The medical device of claim 1, wherein the doubled back portion comprises a radial inner wall defining a lumen of the elongate tubular body and a radial outer wall extending over an outer perimeter of the inner wall.

8. The medical device of claim 1, the elongate tubular body comprising a covering disposed over at least a portion of the elongate tubular body.

9. The medical device of claim 1, wherein the elongate tubular body in the unconstrained configuration is configured to facilitate fluid flow without leakage between the first end portion and the second end portion.

10. The medical device of claim 1, wherein the medical device is a self-expanding stent.

11. The medical device of claim 1, wherein the elongate tubular body comprises a mesh, one or more braided wires, or woven filament.

12. The medical device of claim 1, wherein the elongate tubular body comprises a polymer, a metal, a shape memory material, or Nitinol.

13. A medical device for placement in an anastomosis, comprising:
an elongate tubular body comprising a first end portion, a body portion, and a second end portion opposite the first end portion, the elongate tubular body having a constrained configuration and an unconstrained configuration;
the first end portion, in the unconstrained configuration comprising a retention member, an elongate section distal to the retention member, and a doubled back portion extending from the elongate section over the retention member towards the second end portion,
wherein the doubled back portion has a free proximal end unattached to the body portion of the elongate tubular body, and wherein the elongate section is configured to provide dynamic movement of the retention member relative to the second end portion.

14. The medical device of claim 13, the elongate tubular body comprising a central portion disposed between the first end portion and the second end portion, the second end portion comprising a second retention member and a second doubled back portion extending from the retention member towards the first end portion.

15. The medical device of claim 14, the second end portion comprising a second elongate section distal to the second retention member, wherein the second doubled back portion extends from the second elongate section over the second retention member towards the central portion, and wherein the second elongate section is configured to provide dynamic movement of the second retention member relative to the first end portion.

16. A medical device, comprising:
a stent comprising an elongate tubular body comprising a first end portion, a body portion, and a second end portion opposite the first end portion, the elongate tubular body having a constrained configuration and an unconstrained configuration;
the first end portion, in the unconstrained configuration comprising a retention member, an elongate section distal to the retention member, and a doubled back portion extending from the elongate section over the retention member towards the second end portion; and
a delivery device configured to hold the stent in the constrained configuration and deploy the stent in an anastomosis in the unconstrained configuration;
wherein the doubled back portion has a free proximal end unattached to the body portion of the elongate tubular body.

17. The medical device of claim 16, the elongate tubular body comprising a central portion disposed between the first end portion and the second end portion, the second end portion comprising a second retention member.

18. The medical device of claim 17, the second end portion comprising a second doubled back portion extending from the retention member towards the first end portion.

19. The medical device of claim 18, the second end portion comprising a second elongate section distal to the second retention member, wherein the second doubled back portion extends from the second elongate section over the second retention member towards the central portion.

20. The medical device of claim 16, the second end portion comprising a straight end portion.

\* \* \* \* \*